US012668559B2

(12) United States Patent
Medlock et al.

(10) Patent No.: US 12,668,559 B2
(45) Date of Patent: Jun. 30, 2026

(54) SELECTIVE HYDROGENATION OF ALKYNES TO ALKENES IN THE PRESENCE OF A PHOSPHORUS COMPOUND AND AN ORGANIC SULPHUR COMPOUND

(71) Applicant: DSM IP ASSETS B.V., Heerlen (NL)

(72) Inventors: Jonathan Alan Medlock, Rheinfelden (CH); Lise Malika Molinari, Basel (CH)

(73) Assignee: DSM IP ASSETS B.V., Maastricht (NL)

(*) Notice: Subject to any disclaimer, the term of this patent is extended or adjusted under 35 U.S.C. 154(b) by 591 days.

(21) Appl. No.: 17/613,765

(22) PCT Filed: May 26, 2020

(86) PCT No.: PCT/EP2020/064497

§ 371 (c)(1),
(2) Date: Nov. 23, 2021

(87) PCT Pub. No.: WO2020/239721

PCT Pub. Date: Dec. 3, 2020

(65) Prior Publication Data

US 2022/0242807 A1 Aug. 4, 2022

(30) Foreign Application Priority Data

May 27, 2019 (EP) .................................... 19176760

(51) Int. Cl.

| | |
|---|---|
| ***C07C 29/17*** | (2006.01) |
| ***B01J 23/44*** | (2006.01) |
| ***B01J 27/232*** | (2006.01) |
| ***B01J 35/23*** | (2024.01) |
| ***C07C 33/02*** | (2006.01) |
| ***C07C 33/14*** | (2006.01) |
| ***C07C 33/16*** | (2006.01) |
| ***C07C 323/12*** | (2006.01) |
| ***C07F 9/50*** | (2006.01) |

(52) U.S. Cl.

CPC ............... *C07C 29/17* (2013.01); *B01J 23/44* (2013.01); *B01J 27/232* (2013.01); *B01J 35/23* (2024.01); *C07C 33/02* (2013.01); *C07C 33/14* (2013.01); *C07C 33/16* (2013.01); *C07C 323/12* (2013.01); *C07F 9/50* (2013.01); *C07C 2601/18* (2017.05)

(58) Field of Classification Search

CPC ......... C07C 29/17; C07C 33/02; C07C 33/14; C07C 33/16; C07C 323/12; C07C 2601/18; B01J 35/23; B01J 23/44; B01J 27/232; C07F 9/50

See application file for complete search history.

(56) References Cited

U.S. PATENT DOCUMENTS

| | | | |
|---|---|---|---|
| 3,715,404 A | 2/1973 | Lindlar et al. | |
| 8,530,707 B2 | 9/2013 | Bonrath et al. | |
| 2008/0033221 A1* | 2/2008 | Hori et al. | ............... B01J 23/44 556/136 |

FOREIGN PATENT DOCUMENTS

| | | |
|---|---|---|
| CN | 102131578 | 7/2011 |
| CN | 102503772 | 6/2012 |
| JP | 59-78126 | 5/1984 |
| JP | 10-168021 | 6/1998 |
| JP | 2002-145814 | 5/2002 |
| JP | 2012-500112 | 1/2012 |
| KR | 2011-0051252 | 5/2011 |
| WO | 2010/020671 | 2/2010 |
| WO | 2016/038454 | 3/2016 |

OTHER PUBLICATIONS

International Search Report for PCT/EP2020/064497 mailed Jul. 9, 2020, 3 pages.
Written Opinion of the ISA for PCT/EP2020/064497 mailed Jul. 9, 2020, 6 pages.
Zhang, Tong Sheng et al, "Role of Electron Donors on the Selective Hydrogenation of Conjugated Dienes or Alkyne", ACTA Chemica Sinica, 1993, vol. 51, pp. 490-495 (English Abstract).
Notice of Preliminary Rejection, KR Appln. No. 2021-7042245, Dec. 5, 2023 (English Translation).
Notice of First Examination Opinion, CN Application No. 202080038878.8, Dec. 28, 2023 (English Translation).

* cited by examiner

*Primary Examiner* — Amy C Bonaparte
*Assistant Examiner* — Derek Rhoades
(74) *Attorney, Agent, or Firm* — NIXON & VANDERHYE P.C.

(57) ABSTRACT

The present invention relates to a process of hydrogenating an alkyne selectively to an alkene by hydrogen using a hydrogenation catalyst which is palladium supported on a carrier in the presence of an additive mixture of an organic phosphorus compound (AP) and an organic sulphur compound (AS).

15 Claims, No Drawings

SELECTIVE HYDROGENATION OF ALKYNES TO ALKENES IN THE PRESENCE OF A PHOSPHORUS COMPOUND AND AN ORGANIC SULPHUR COMPOUND

This application is the U.S. national phase of International Application No. PCT/EP2020/064497 filed May 26, 2020 which designated the U.S. and claims priority to EP patent application Ser. No. 19/176,760.7 filed May 27, 2019, the entire contents of each of which are hereby incorporated by reference.

TECHNICAL FIELD

The present invention relates to the hydrogenation of alkynes to alkenes.

BACKGROUND OF THE INVENTION

Alkynes can be hydrogenated to alkenes by hydrogen in the presence of noble metal catalysts. Palladium catalysts can be used for the hydrogenation of alkynes to alkenes.

An important type of alkynes are alkynols and an important type of alkenes are alkenols. Alkynols or the alkenols, respectively, are substances which are produced on an industrial scale and are of high importance, particularly for the field of vitamins and aroma chemicals. A non-exhaustive list of such important alkynols and alkenols are 2-methylbut-3-yn-2-ol, 2-methylbut-3-en-2-ol, 3,7-dimethyloct-6-en-1-yn-3-ol, 3,7-dimethylocta-1,6-dien-3-ol, 3,7,11,15-tetramethylhexadec-1-yn-3-ol and 3,7,11,15-tetramethylhexadec-1-en-3-ol.

In the hydrogenation of alkynes and alkynols there exist several problems. One problem is that next to the carbon-carbon triple bond also other chemical groups being eventually present might be hydrogenated. To a certain extent this problem can be solved by using protecting groups. This, however, requires additional steps of protection and deprotection which is not favourable in view of additional time, cost and waste formation.

Another problem is that the selectivity at high conversion is not sufficiently high. As in any chemical reaction, the target is to have transformed as much as possible of the starting material into the desired product. In the present case, there is a further drive to obtain as high conversion as possible, because the alkyne, respectively the alkynol, i.e. the starting material, and the alkenol, i.e. the product of the selective hydrogenation, are very difficult to separate. Hence, running reactions at partial conversion followed by separation of the unreacted starting material and repeating the reaction is very difficult.

A particular problematic aspect in the selective hydrogenation of alkynes, respectively alkynols, is the over-hydrogenation. Over-hydrogenation describes the effect that the hydrogenation of alkynes, respectively alkynols does not stop at the stage of alkenes, respectively alkenols, but continues to yield significant amounts of alkanes, respectively alkanol, i.e. that the hydrogenation reaction does not selectively only hydrogenate the carbon-carbon triple bond to the carbon-carbon double bond, but that the carbon-carbon double bond is also hydrogenated to a carbon-carbon single bond in significant amounts. The over-hydrogenated compound can be very difficult to be separated from the desired products.

Lindlar discloses in U.S. Pat. No. 2,681,938 a selective hydrogenation of alkynes to alkenes using a palladium catalyst which is modified by lead or bismuth.

In U.S. Pat. No. 3,715,404 a selective hydrogenation is disclosed using a palladium catalyst which is partially deactivated by some specific organic sulphur compounds.

WO 2016/038454 A1 discloses a process of hydrogenating acetylene selectively to ethylene using a hydrogenation catalyst which is palladium supported on a carrier in the presence of triphenyl phosphine sulphide.

Furthermore, the hydrogenation of alkynes, particularly of alkynols, leads to the formation of undesired side products, such as the formation of dimers or oligomers derived from the alkyne or the alkene, respectively the alkynol or the alkenol.

SUMMARY OF THE INVENTION

Therefore, the problem to be solved by the present invention is to offer a process for the hydrogenation of alkynes, particularly of alkynols, selectively to an alkene, particularly to an alkenol, which yields high conversion, high selectivity and low over-hydrogenation.

Surprisingly, the process according to claim 1 has offered a solution to this problem. It has been found that particularly the use of additives having 2 or more phosphino groups are very advantageous in offering this combination of desired properties.

Further aspects of the invention are subject of further independent claims. Particularly preferred embodiments are subject of dependent claims.

DETAILED DESCRIPTION OF THE INVENTION

In a first aspect the present invention relates to a process of hydrogenating an alkyne selectively to an alkene using a hydrogenation catalyst which is palladium supported on a carrier in the presence of an additive mixture of

- at least one additive (AP) which is an organic phosphorus compound; and
- at least one additive (AS) which is an organic sulphur compound;

wherein the alkyne comprises at least one carbon-carbon triple bond and that said at least carbon-carbon triple bond is selectively hydrogenated to a respective carbon-carbon double bond to form said alkene.

For sake of clarity, some terms as been used in the present document are defined as follows:

In the present document, a "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example $-CH(CH_3)-CH_2-CH_3$ is considered as a $C_4$-alkyl group.

Any wavy line in any formula of this document represents a carbon-carbon bond which when linked to the carbon-carbon double bond is either in the Z- or in the E-configuration.

In case identical labels for symbols or groups are present in several formulae, in the present document, the definition of said group or symbol made in the context of one specific formula applies also to other formulae which comprises the same said label.

In the present document, an "alkyne" is a chemical compound which has at least one carbon-carbon triple bond in its chemical formula. The alkyne may comprise at least one further/additional chemical functional group, particularly hydroxyl group(s) and/or carbon-carbon double bond(s).

In the present document, an "alkynol" is a chemical compound which has at least one carbon-carbon triple bond and at least one hydroxyl group in its chemical formula. In other words, an alkynol is a hydroxy functionalised alkyne.

Analogously, an "alkene" is a chemical compound which has at least one carbon-carbon double bond in its chemical formula. The alkene may comprise at least one further/additional chemical functional group, particularly hydroxyl group(s).

An "alkenol" is a chemical compound which has at least one carbon-carbon double bond and at least one hydroxyl group in its chemical formula. In other words, an alkenol is a hydroxy functionalised alkene.

In the present document a "hydrocarbyl" group is a univalent group which formally is formed by removing a hydrogen atom from a hydrocarbon.

Alkyne

In this process an alkyne is selectively hydrogenated to the respective alkene.

It is important for the present invention that the hydrogenation is selective, that is reducing the carbon-carbon triple bond to the respective carbon-carbon double bond. In other words, other chemical groups which might be present in the alkyne are not modified by said hydrogenation reaction. Particularly, the hydrogenation is selective also in that sense that the carbon-carbon double bond of the alkene is not, or at least not significantly, further hydrogenated to a carbon-carbon single bond ("over-hydrogenation").

It, furthermore, has been observed that—besides the reduced formation of over-hydrogenated products—also the formation of other side products, such as formation of dimers or oligomers derived from the starting material or products, are significantly reduced by the above process.

In one embodiment, the alkyne is preferably a hydrocarbon having at least one carbon-carbon triple bond and optionally at least one carbon-carbon double bond. Preferably, in this embodiment said alkyne has aromatic substituents. The alkyne has preferably the formula (A)

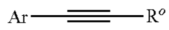

(A)

wherein Ar represents an aromatic group, which can further bear some alkyl or alkenyl groups; and wherein $R^0$ is either H or an alkyl, preferably a $C_{1-4}$-alkyl group, or an alkenyl group, preferably a $C_{1-4}$-alkenyl group, or $Ar^1$, wherein $Ar^1$ represents an aromatic group, which can further bear some alkyl, preferably $C_{1-4}$-alkyl, or alkenyl, preferably $C_{1-4}$-alkenyl, groups. It is preferred that $Ar^1$=Ar. It is further preferred that Ar is a phenyl group.

Preferably, the alkyne of formula (A) is phenylacetylene (=ethynyl-benzene) or diphenylacetylene (=1,2-diphenylethyne=tolane).

The alkyne preferably further comprises at least one additional chemical functional group, particularly at least one hydroxyl group and/or at least one carbon-carbon double bond; wherein the at least further chemical functional group remains unchanged by the hydrogenation.

In a very preferred embodiment, the alkyne is an alkynol. Preferably, the alkynol is an alkynol which has a hydroxyl group attached to a carbon which is in alpha position to the carbon-carbon triple bond of the alkynol, i.e. the alkynol is preferably an alpha-alkynol.

The alkynol has preferably a following structural element

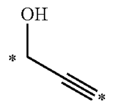 [SMILES: *#CCO]

in its structural formula, where * signifies the position(s) of further substituent(s).

In an even more preferred embodiment, the alkynol is an alkynol in which the carbon-carbon triple bond is a terminal carbon-carbon triple bond.

In a very preferred embodiment the alkynol has a following structural element

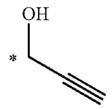

in its structural formula where * signifies the position of further substituent(s).

In a very preferred embodiment the alkyne is an alkynol, and said alkynol is an alkynol of the formula (I)

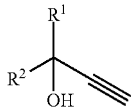

(I)

wherein either $R^1$ represents H or a methyl or ethyl group, preferably a methyl or ethyl group; and $R^2$ represents a saturated or unsaturated linear or branched or cyclic hydrocarbyl group with 1 to 46 C atoms which optionally comprises at least one chemical functional group, particularly at least one hydroxyl group;

or $R^1$ and $R^2$ represent together an alkylene group forming a 5 to 7 membered ring;

with the proviso that $R^1$ has the same meaning in formulae (I) and (II) and that $R^2$ has the same meaning in formulae (I) and (II).

In formula (I) the preferred substituent $R^1$ is a methyl group.

It is further preferred that in formula (I) the substituent $R^2$ is a methyl group.

A very preferred alkynol of formula (I) is 2-methylbut-3-yn-2-ol (i.e. $R^1$=$R^2$=methyl).

In another embodiment, $R^1$ and $R^2$ represent together an alkylene group forming a 5 to 7 membered ring. The alkylene group may be linear or branched and optionally comprises at least one chemical functional group, and/or is olefinically unsaturated.

Preferably the alkylene group is a pentylene group. One of the preferred alkynols of this embodiment is 1-ethynyl-cyclohexan-1-ol.

In another preferred embodiment the substituent is $R^2$ is selected from the group consisting of formula (R2-I), (R2-II), (R2-III), (R2-IV), (R2-V), (R2-VI) and (R2-VII)

(R2-I)

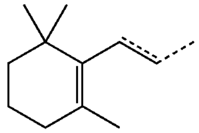

(R2-II)

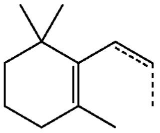

(R2-III)

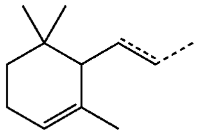

(R2-IV)

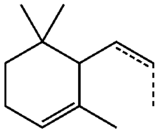

(R2-V)

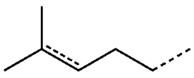

(R2-VI)

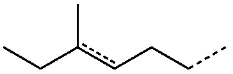

(R2-VII)

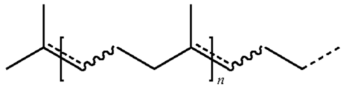

wherein the dotted line represents the bond by which the substituent of formula (R2-I), (R2-II), (R2-III), (R2-IV), (R2-V), (R2-VI) or (R2-VII) is bound to the rest of the compound of formula (I) or formula (II);

and wherein any bond having dotted line (═) represents independently from each other either a single carbon-carbon bond or a double carbon-carbon bond;

and wherein any wavy line represents independently from each other a carbon-carbon bond which when linked to the carbon-carbon double bond is either in the Z or in the E-configuration;

and wherein n represents 1, 2, 3, 4, 5 or 6, particularly 1 or 2 or 3, preferably 3 or 2, most preferably 2.

The alkynol is preferably an alkynol which is selected from the group consisting of 3-methyl-5-(2,6,6-trimethylcyclohex-1-en-1-yl)pent-1-yn-3-ol, (E)-3-methyl-1-(2,6,6-trimethylcyclohex-1-en-1-yl)pent-1-en-4-yn-3-ol, (Z)-3-methyl-1-(2,6,6-trimethylcyclohex-1-en-1-yl)pent-1-en-4-yn-3-ol, (E/Z)-3-methyl-1-(2,6,6-tri-methylcyclohex-1-en-1-yl)pent-1-en-4-yn-3-ol, 3-methyl-5-(2,6,6-trimethylcyclohex-2-en-1-yl)pent-1-yn-3-ol, (E)-3-methyl-1-(2,6,6-trimethylcyclohex-2-en-1-yl)pent-1-en-4-yn-3-ol, (Z)-3-methyl-1-(2,6,6-trimethylcyclohex-2-en-1-yl)pent-1-en-4-yn-3-ol, 3,7-dimethyloct-6-en-1-yn-3-ol, 3,7-dimethyloct-1-yn-3-ol, (E)-3,7-dimethylnon-6-en-1-yn-3-ol, (Z)-3,7-dimethylnon-6-en-1-yn-3-ol, (E/Z)-3,7-di-methylnon-6-en-1-yn-3-ol, 3,7-dimethylnon-1-yn-3-ol, 3,7,11-trimethyldodec-1-yn-3-ol, (E)-3,7,11-trimethyldodec-6-en-1-yn-3-ol, (Z)-3,7,11-trimethyldodec-6-en-1-yn-3-ol, (E/Z)-3,7,11-trimethyldodec-6-en-1-yn-3-ol, 3,7,11-trimethyldodec-10-en-1-yn-3-ol, (E)-3,7,11-trimethyldodeca-6,10-dien-1-yn-3-ol, (Z)-3,7,11-trimethyldo-deca-6,10-dien-1-yn-3-ol, (E/Z)-3,7,11-trimethyldodeca-6,10-dien-1-yn-3-ol, 3,7,11,15-tetramethylhexadec-1-yn-3-ol, (E)-3,7,11,15-tetramethylhexadec-6-en-1-yn-3-ol, (Z)-3,7,11,15-tetramethylhexadec-6-en-1-yn-3-ol, (E/Z)-3,7,11,15-tetramethylhexadec-6-en-1-yn-3-ol, (E)-3,7,11,15-tetramethylhexadec-10-en-1-yn-3-ol, (Z)-3,7,11,15-tetramethylhexadec-10-en-1-yn-3-ol, (E/Z)-3,7,11,15-tetramethylhexadec-10-en-1-yn-3-ol, 3,7,11,15-tetramethylhexadec-14-en-1-yn-3-ol, (6E,10E)-3,7,11,15-tetramethylhexadeca-6,10-dien-1-yn-3-ol, (6E,10Z)-3,7,11,15-tetramethylhexadeca-6,10-dien-1-yn-3-ol, (6Z,10E)-3,7,11,15-tetramethylhexa-deca-6,10-dien-1-yn-3-ol, (6Z,10Z)-3,7,11,15-tetramethylhexadeca-6,10-dien-1-yn-3-ol, (E)-3,7,11,15-tetramethylhexadeca-10,14-dien-1-yn-3-ol, (Z)-3,7,11,15-tetramethylhexadeca-10,14-dien-1-yn-3-ol, (6E,10E/Z)-3,7,11,15-tetramethylhexa-deca-6,10-dien-1-yn-3-ol, (6Z,10E/Z)-3,7,11,15-tetramethylhexadeca-6,10-dien-1-yn-3-ol, (6E/Z,10E)-3,7,11,15-tetramethylhexadeca-6,10-dien-1-yn-3-ol, (6E/Z,10Z)-3,7,11,15-tetramethylhexadeca-6,10-dien-1-yn-3-ol, (6E/Z,10E/Z)-3,7,11,15-tetramethylhexadeca-6,10-dien-1-yn-3-ol, (E)-3,7,11,15-tetramethyl-hexadeca-6,14-dien-1-yn-3-ol, (Z)-3,7,11,15-tetramethylhexadeca-6,14-dien-1-yn-3-ol, (E/Z)-3,7,11,15-tetramethylhexadeca-6,14-dien-1-yn-3-ol, (E)-3,7,11,15-tetra-methylhexadeca-10,14-dien-1-yn-3-ol, (Z)-3,7,11,15-tetramethylhexadeca-10,14-dien-1-yn-3-ol, (E/Z)-3,7,11,15-tetramethylhexadeca-10,14-dien-1-yn-3-ol, (6E,10E)-3,7,11,15-tetramethylhexadeca-6,10,14-trien-1-yn-3-ol, (6E,10Z)-3,7,11,15-tetramethylhexadeca-6,10,14-trien-1-yn-3-ol, (6Z,10E)-3,7,11,15-tetra-methylhexadeca-6,10,14-trien-1-yn-3-ol, (6Z,10Z)-3,7,11,15-tetramethylhexadeca-6,10,14-trien-1-yn-3-ol, (6E,10E/Z)-3,7,11,15-tetramethylhexadeca-6,10,14-trien-1-yn-3-ol, (6E/Z,10E)-3,7,11,15-tetramethylhexadeca-6,10,14-trien-1-yn-3-ol, (6Z,10E/Z)-3,7,11,15-tetramethylhexadeca-6,10,14-trien-1-yn-3-ol, (6E/Z,10Z)-3,7,11,15-tetramethylhexadeca-6,10,14-trien-1-yn-3-ol, and (6E/Z,10E/Z)-3,7,11,15-tetramethylhexadeca-6,10,14-trien-1-yn-3-ol.

Hydrogenation Catalyst

The process uses a hydrogenation catalyst which is palladium supported on a carrier.

Such hydrogenation catalysts are principally known to the person skilled in the art. Palladium is a noble metal. In the present invention Palladium is supported on a carrier, i.e. palladium is attached to/or deposited on a carrier. The carrier is a solid material.

Preferably said carrier is carbon or an inorganic carrier. Preferred inorganic carriers are oxides or carbonates. Preferred oxides are oxides of silicon, aluminum or titanium or cerium. Particularly preferred are silicon dioxide, alumina and titanium dioxide and ceria.

Silicon dioxide can be used as pyrogenic silica or precipitated or ground silica as carrier. Preferably silicon dioxide used as carrier is pyrogenic or precipitated silica. Most preferred silicon dioxide is a silicon dioxide which is essential pure $SiO_2$. In other words, it is preferred that the silicon dioxide carrier consists of more than 95%, more preferably more than 98%, even more preferred more than 99%, by weight of $SiO_2$.

Calcium carbonate is the preferred carbonate. Preferred calcium carbonate is precipitated calcium carbonate.

It is possible that carrier as used is a mixed oxide.

In addition, the supported palladium catalyst can be doped with other metals, for example lead. A well-known catalyst of this type is the "Lindlar catalyst" which is palladium on calcium carbonate doped with lead. Such Lindlar catalysts are for example commercially available from Sigma-Aldrich, Evonik, Johnson-Matthey or Hindustan Platinum.

More preferred hydrogenation catalysts are palladium on carbon, palladium on silica and palladium on alumina and palladium on a carbonate; even more preferred is palladium on calcium carbonate, most preferred is palladium on calcium carbonate doped with lead.

The amount of palladium in the hydrogenation catalyst is preferably in the range of from 0.5 to 20 weight %, more preferably in the range of from 2 to 5 weight %, most preferably in the range of approximately 5 weight %, based on the total weight of the hydrogenation catalyst.

In one the embodiment, the hydrogenation catalyst is used in the form of a colloidal suspension.

Very suitable hydrogenation catalysts are catalysts as they are disclosed in WO 2009/096783 A1 or in Peter T. Witte et al., Top Catal (2012) 55:505-511 and commercialized by BASF under the trade name NanoSelect™.

In another preferred embodiment, the hydrogenation catalyst does not comprise any contain organic any quaternary ammonium compounds.

Additive Mixture

The process is performed in the presence of an additive mixture. Said additive mixture is a mixture of at least one additive (AP) which is an organic phosphorus compound and at least one additive (AS) which is an organic sulphur compound.

It is important to stress that the additive mixture of additive (AP) and additive (AS) is a mixture of two different additives, in other words, an additive having P and S in the same molecule such as triphenylphosphine sulphide ($Ph_3P{=}S$) is not considered as a mixture of an additive (AP) and additive (AS) in this document. Furthermore, it is to be stressed that such a molecule (having P and S in the same molecule) is also not considered to be either an additive (AP) which is an organic phosphorus compound or an additive (AS) which is an organic sulphur compound.

Additive (AP)

The additive (AP) which is an organic phosphorus compound preferably bears either a phosphino or a phosphine oxide group.

The additive (AP) which is an organic phosphorus compound comprises no sulphur atoms.

In case of the additive (AP) bears a phosphine oxide group, it is preferred that said additive has one or two, more preferred one, phosphine oxide group(s).

Particularly preferred as additive (AP) which is an organic phosphorus compound bearing a phosphine oxide is diphenylphosphine oxide.

In case of the additive (AP) bears a phosphino group the additive is a phosphine. It is preferred that said additive (AP) has 1 or more, preferably 1 to 4, more preferably 1 to 3, phosphino group(s).

In one of the embodiments, it is preferred that the additive (AP) has one phosphino groups of the formula (III)

(III)

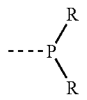

wherein R is either an alkyl group or a cycloalkyl group or an aryl group, particularly a phenyl or a tolyl group and wherein the dotted line represents the bond by which the substituent of formula (III) is bound to the rest of the additive (AP).

The alkyl group is preferably a $C_{1-6}$-alkyl group. The cycloalkyl group is preferably a $C_{5-8}$-cycloalkyl group.

In one of the embodiments, which is a preferred embodiment, it is preferred that the additive (AP) has more than one, preferably two, phosphino groups of the formula (III)

(III)

wherein R is either an alkyl group or a cycloalkyl group or an aryl group, particularly a phenyl or a tolyl group and wherein the dotted line represents the bond by which the substituent of formula (III) is bound to the rest of the additive (AP).

The alkyl group is preferably a $C_{1-6}$-alkyl group. The cycloalkyl group is preferably a $C_{5-8}$-cycloalkyl group.

In a preferred embodiment the additive (AP) is selected from the group consisting of tricyclohexyl phosphine, triphenylphosphine, tri-orthotolylphosphine, 1,2-bis(diphenylphosphino)ethane, 1,3-bis(diphenylphosphino)propane, 1,4-bis(di-phenylphosphino)butane, 1,3-bis(diphenylphosphino)-2-(diphenylphosphino)-methyl-2-methylpropane, 2,2'-bis(diphenylphosphino)-1,1'-binaphthalene, bis(2-diphenylphosphinoethyl)phenylphosphine and 1,1'-bis(diphenylphosphino)-ferrocene, preferably selected from the group consisting of triphenylphosphine, 1,2-bis(diphenylphosphino)ethane and 1,3-bis(diphenylphosphino)propane.

Additive (AS)

The additive (AS) which is an organic sulphur compound is preferably an organic sulphur compound is selected from the group consisting of thiol, thioether and disulphide.

The additive (AS) comprises no phosphor atoms.

A thiol carries at least one mercapto group (SH). In one embodiment the thiol carries one SH group. Particular suitable thiols of this embodiment are alkylmercaptans, particularly n-butylmercaptan or n-hexylmercaptan; monothio alcohols, particularly monothioglycols, monothioglycerols, monothioethylene-glycols, monothiopropyleneglycols, monothiopolyethyleneglycols, monothiolpolypropyleneglycols, monothioethanol or monothiopropanol; aromatic thiophenols, particularly thiophenol, thiocresol, mercaptopyridine or mercaptopyrimidine.

In another embodiment the thiol is a polythiol which carries two or more mercapto groups (SH). A first group of preferred polythiols are aromatic polythiols. Preferably, the SH groups are preferably bound directly on an aromatic hydrocarbon (thiophenols). The aromatic hydrocarbon may have one or several aromatic rings. The aromatic rings can form a fused ring system or can be separated by spacers for example by alkylene groups or by functional groups. The SH groups may be bound directly on the same aromatic ring or on different aromatic rings. Particularly preferred as aromatic polythiols are 4,4'-dimercaptobi-phenyl or 4,4'-thiodibenzenethiol or dithioresorcinol or dithiotoluene.

A thioether carries at least one structural element —S— which is bound to two carbon atoms in its chemical formula. The thioether can be a symmetric or an asymmetric thioether.

Examples for suitable thioethers are particularly selected from the group consisting of dialkylthioether, particularly di-n-butyl thioether or di-tertiary butyl thioether; dihydroxy-alkylthioether, particularly thiodiethyleneglycol ($S(CH_2CH_2OH)_2$) or thiodipropyleneglycol; diarylthioether, particularly diphenyl thioether; diaralkyl thioether, particularly, dibenzyl thioether; alkylaryl thioether, particularly thioanisole; cyclic thioethers, and substituted derivatives thereof, particularly ethylene sulfide, thiophene, thiazole, thiopyran, thioxanthone, thioxanthydrol, 1,4-thioxane; and alkylheteroaryl thioether, particularly 2-methyl-thio-4,6-di-amino pyrimidine.

In a preferred embodiment the thioether contains at least two thioether groups in the molecule.

In one of the embodiments, the thioether has the following formula (XI):

$$R^oS-[E-S]_{n1}-E-SR^0 \quad (XI)$$

wherein E represents a linear or branched $C_{1-6}$-alklyene group, and n1 represents an integer from 0 to 4, particularly 0 or 1;

and $R^0$ represents an $C_{1-6}$-alkyl group, preferably a methyl or ethyl group.

E represents preferably an ethylene or a propylene group.

In this embodiment, the thioether is preferably 1,3-bis(methylthio)propane

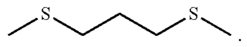

In a preferred embodiment the thioether bears at least one hydroxyl group, preferably two hydroxyl group.

In a preferred embodiment the thioether contains at least two thioether groups in the molecule.

particularly having the following formula (XII):

$$HO-D-S-[D-S]_{n2}-D-OH \quad (XII)$$

wherein D represents a linear or branched $C_{1-6}$-alklyene group, and n2 represents an integer from 1 to 4, particularly 1 or 2.

The compounds of Formula (XII) can be obtained by the reaction of one mole of α,ω-dihalogenoalkane, or the respective α,ω-dihalogenoalkanethioether, with 2 moles of a mono-thio alkyleneglycol.

In a most preferred embodiment, the thioether is 2,2'-(ethane-1,2-diylbis(sulfanediyl))bis(ethan-1-ol)

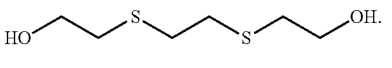

A disulphide carries at least one structural element —S—S— which is bound to two carbon atoms in its chemical formula. The disulphide can be a symmetric or an asymmetric disulphide.

Examples for suitable disulphide are particularly selected from the group consisting of dialkyl disulphides, particularly di-n-butyl disulphide; diaryl disulphides, particularly diphenyl disulphide, di-(o-carboxyphenyl)-disulphides, and diaralkyl disulphides, particularly, dibenzyl disulphide.

The disulfide compounds can be obtained from the respective thiols by the action of mild oxidation agents.

It is mostly preferred that one additive (AS) which is an organic sulphur compound is a thioether bearing at least one hydroxyl group, and is particularly 2,2'-(ethane-1,2-diylbis(sulfanediyl))bis(ethan-1-ol)

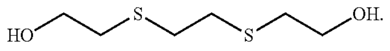

The additive mixture is preferably a mixture of at least one additive (AP) which is an organic phosphorus compound, which has one or more than one phosphino groups of the formula (III)

(III)

wherein R is either an alkyl group or a cycloalkyl group or an aryl group, particularly a phenyl or a tolyl group and wherein the dotted line represents the bond by which the substituent of formula (III) is bound to the rest of the additive (AP);

preferably selected from the group consisting of tricyclohexyl phosphine, triphenylphosphine, tri-ortho-tolylphosphine, 1,2-bis(diphenyl-phosphino)ethane, 1,3-bis(diphenylphosphino)propane, 1,4-bis(di-phenylphosphino)butane, 1,3-bis(diphenylphosphino)-2-(diphenylphos-phino)methyl-2-methylpropane, 2,2'-bis(diphenylphosphino)-1,1'-bi-naphthalene, bis(2-diphenylphosphinoethyl)phenylphosphine and 1,1'-bis(diphenylphosphino)ferrocene, more preferably selected from the group consisting of triphenyl-phosphine, 1,2-bis(diphenylphosphino)ethane and 1,3-bis(di-phenylphosphino)propane;

and at least one additive one additive (AS) which is an organic sulphur compound, which is selected from the group consisting of thiol, thioether and disulphide preferably is a thioether, more preferably is a thioether bearing at least one hydroxyl group; most preferably is 2,2'-(ethane-1,2-diylbis(sulfanediyl))-bis(ethan-1-01).

The additive mixture is most preferably a mixture of at least one additive (AP) which is selected from the group consisting of triphenylphosphine, 1,2-bis(diphenylphosphino)ethane and 1,3-bis(diphenylphosphino)propane; and at least one thioether bearing at least one hydroxyl group, preferably 2,2'-(ethane-1,2-diylbis(sulfanediyl))bis(ethan-1-ol).

It is preferred that the molar ratio of the additive (AP) to the additive (AS) is in the range of 10:1-1:10, preferably of 5:1-1:5, even more preferably of 2:1-1:2.

The additives (AP) and/or (AS) can be added individually or as a mixture to the alkyne, particularly to the alkynol, or as a pre-solution to the alkyne, particularly to the alkynol, before the beginning of the hydrogenation reaction or during the hydrogenation process. In case of a pre-solution or a pre-mixture the additive (AP) and/or (AS) is dissolved or dispersed in a small amount of an organic solvent or, preferably, of the alkyne, particularly of the alkynol.

The above described process yields selectively the respective alkene, or the alkenol in the case of the preferred embodiment of the alkyne being an alkynol. Said alkene, respectively alkenol, has the same chemical structure as the alkyne, respectively the alkynol, with the exception that the carbon-carbon triple bond is in the alkene, respectively alkenol, a carbon-carbon double bond.

In other words, when in the preferred case the alkynol of formula (I)

(I)

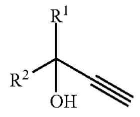

is hydrogenated, the alkenol formed by the selective hydrogenation is the alkenol of formula (II)

(II)

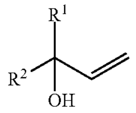

with the proviso that $R^1$ has the same meaning in formulae (I) and (II) and that $R^2$ has the same meaning in formulae (I) and (II).

It is preferred that the weight ratio of the additive mixture to catalyst is in the range of 0.01:1-100:1, preferably of 0.1:1-10:1, and more preferably of 0.2:1-3:1.

The amount of hydrogenation catalyst (i.e. sum of palladium and carrier) is preferably in the range of from 0.0001 to 10% by weight %, more preferably in the range of from 0.001 to 1% by weight, most preferably in the range of from 0.01 to 0.1% by weight, based on the weight of the alkyne.

The amount of palladium is preferably 1 to 10% by weight, preferably 3 to 7% by weight, based on the weight of the hydrogenation catalyst.

The hydrogenation reaction is preferably carried out at a temperature in the range of from 10 to 150° C., more preferably at a temperature in the range of from 20 to 100° C., most preferably at a temperature in the range of from 40 to 90° C.

The hydrogenation reaction is preferably carried out at a hydrogen pressure in the range of from 1 to 25 bara (bar absolute) hydrogen, more preferably at a hydrogen pressure in the range of from 2 to 10 bara hydrogen, even more preferably at a hydrogen pressure in the range of from 2 to 6 bara hydrogen, further more preferably at a hydrogen pressure in the range of from 2.5 to 4 bara hydrogen most preferably at a hydrogen pressure in the range of from 2.5 to 3 bara hydrogen.

The hydrogenation reaction can be carried out without solvent or in the presence of an organic solvent. The organic solvent is preferably selected from the group consisting of hydrocarbons, halogenated hydrocarbons, alcohols, ethers, esters, carbonates, amides, nitriles and ketones and mixtures thereof. More preferred are $C_{4-10}$ aliphatic hydrocarbons, $C_{6-10}$ aromatic hydrocarbons, $C_{6-10}$ aromatic hydrocarbons substituted with one or more $C_{1-4}$ linear alkyl groups or $C_{3-4}$ branched alkyl groups or halogens, $C_{1-4}$ linear alcohols or $C_{3-4}$ branched alcohols, acyclic and cyclic $C_{4-10}$ ethers, $C_{3-10}$ esters, $C_{3-10}$ ketones and mixtures thereof. Especially preferred organic solvents are selected from the group consisting of hexane, heptane, toluene, methanol, ethanol, n-propanol, 2-propanol, n-butanol, tert.-butanol, tetrahydrofuran, 2-methyl-tetrahydrofuran, dioxane, ethyl acetate, isopropyl acetate, ethylene carbonate, propylene carbonate, acetone, and mixtures thereof. The most preferred solvent is heptane.

Preferably, however, the hydrogenation is performed in the absence of any organic solvents.

In a preferred embodiment the hydrogenation is performed in the absence of any organic quaternary ammonium compounds.

In a very much preferred embodiment, the hydrogenation is performed in the absence of any organic solvent and of any organic quaternary ammonium compound.

The above described process yields selectively the respective alkene or the respective alkenol in the case of the alkyne being used as starting material is an alkynol. Said alkene has the same chemical structure as the alkyne with the exception that the carbon-carbon triple bond is in the alkene a carbon-carbon double bond. Accordingly, said alkenol has the same chemical structure as the alkynol with the exception that the carbon-carbon triple bond is in the alkenol a carbon-carbon double bond.

In other words, when in the preferred case the alkynol of formula (I)

(I)

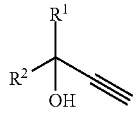

is hydrogenated, the alkenol formed by the selective hydrogenation is the alkenol of formula (II)

(II)

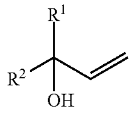

with the proviso that $R^1$ has the same meaning in formulae (I) and (II) and that $R^2$ has the same meaning in formulae (I) and (II).

It has been found that the above process of hydrogenating an alkyne selectively to an alkene, respectively hydrogenating an alkynol selectively to an alkenol, that offers at the same time a very high selectivity and very low over-hydrogenation at a very high conversion.

In a further aspect, the present invention relates to a composition comprising

- an alkyne;
- a hydrogenation catalyst which is palladium supported on a carrier; and
- at least one additive (AP) which is an organic phosphorus compound; and
- at least one additive (AS) which is an organic sulphur compound.

The alkyne, the hydrogenation catalyst as well as the additives (AP) and (AS) have been disclosed and discussed in great detail above.

Therefore, in a preferred embodiment said composition comprises a compound of formula (I)

(I)

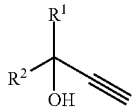

wherein either $R^1$ represents H or a methyl or ethyl group, preferably a methyl or ethyl group; and $R^2$ represents a saturated or unsaturated linear or branched or cyclic hydrocarbyl group with 1 to 46 C atoms which optionally comprises at least one chemical functional group, particularly at least one hydroxyl group;

or $R^1$ and $R^2$ represent together an alkylene group forming a 5 to 7 membered ring;

a hydrogenation catalyst which is palladium supported on a carrier; and at least one additive (AP) which is an organic phosphorus compound; and at least one additive (AS) which is an organic sulphur compound.

Said composition is as also disclosed before very suitable to be hydrogenated by molecular hydrogen and yields in very high selectivity the corresponding alkyne, respectively the alkenol of the formula (II)

(II)

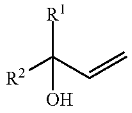

EXAMPLES

The present invention is further illustrated by the following experiments. List of additives used for the examples:

| | |
|---|---|
| AS1 | 2,2'-(ethane-1,2-diylbis(sulfanediyl))bis(ethan-1-ol) |
| AP1 | triphenylphosphine |
| AP2 | 1,2-bis(diphenylphosphino)ethane |
| AP3 | 1,3-bis(diphenylphosphino)propane |
| ASP | Triphenylphosphine sulfide ($Ph_3P{=}S$) |

Selective Hydrogenation Series 1:

Hydrogenation of methylbut-3-yn-2-ol to methylbut-3-en-2-ol

The hydrogenation catalyst (80 mg, palladium-lead on calcium carbonate, containing 5 weight % palladium) was placed in a 500 ml pressure reactor. The respective additives in the amount as given in table 1 and a total of 270 g 2-methylbut-3-yn-2-ol were added to the reactor. The vessel was sealed and purged with nitrogen 3 times (pressurise to 6 bara and release). The reactor was heated to 70° C. and purged with hydrogen 3 times (pressurise to 4 bara and release). The reactor was pressurised to 2.5 bara and the mixture was stirred. The mixture was sampled multiple times near the end of the reaction to determine when the conversion had usually reached>99.9%. Samples were analysed by GC (area %) to determine the selectivity.

TABLE 1

Hydrogenation of methylbut-3-yn-2-ol.

| Example | Additive | Amount [mg] | Conversion [%] | Selectivity[2] [%][1] | Over-Hyd* [%][1] | Dimer/ Oligo# [%][1] |
|---|---|---|---|---|---|---|
| Ref. 1 | None | | >99.9 | 94.9 | 1.7 | 3.4 |
| Ref. 2 | AS1 | 25 | >99.9 | 95.7 | 0.8 | 3.5 |
| Ref. 3 | ASP | 40 | >99.9 | 96.0 | 1.2 | 3.0 |
| 1 | AS1 | 25 | >99.9 | 96.8 | 0.6 | 2.6 |
| | AP1 | 72 | | | | |
| 2 | AS1 | 25 | >99.9 | 97.7 | 1.0 | 1.1 |
| | AP2 | 55 | | | | |
| 3 | AS1 | 25 | 99.2 | 97.5 | 0.8 | 0.9 |
| | AP3 | 56 | | | | |
| 4 | AS1 | 12.5 | >99.9 | 96.5 | 0.8 | 2.7 |
| | AP1 | 36 | | | | |
| 5 | AS1 | 12.5 | >99.9 | 97.4 | 1.1 | 1.5 |
| | AP2 | 28 | | | | |
| 6 | AS1 | 12.5 | >99.9 | 97.7 | 0.9 | 1.2 |
| | AP3 | 28 | | | | |
| 7 | AS1 | 12.5 | >99.9 | 97.8 | 1.1 | 1.1 |
| | AP3 | 43 | | | | |
| 8 | AS1 | 12.5 | >99.9 | 98.0 | 0.8 | 1.1 |
| | AP3 | 34 | | | | |

[1]determined by GC in area %

[2]selectivity: amount of alkenol in the final reaction mixture

*Over-Hyd = over-hydrogenation: methylbutan-2-ol determined by GC in area %

#Dimer/Oligo = side products (mainly dimer/oligomer) determined by GC in area %

Selective Hydrogenation Series 2:

Hydrogenation of 3,7-dimethyloct-6-en-1-yn-3-ol to 3,7-dimethylocta-1,6-dien-3-ol The hydrogenation catalyst (56 mg, palladium-lead on calcium carbonate, containing 5 weight % palladium) was placed in a 500 ml pressure reactor. The respective additives in the amount as given in table 2 and a total of 250 g 3,7-dimethyloct-6-en-1-yn-3-ol were added to the reactor. The vessel was sealed and purged with nitrogen 3 times (pressurise to 6 bara and release). The reactor was heated to 55° C. and purged with hydrogen 3 times (pressurise to 4 bara and release). The reactor was pressurised to 3 bara and the mixture was stirred. The mixture was sampled multiple times near the end of the reaction to determine when the conversion had reached>99.9%. Samples were analysed by GC (area %) to determine the selectivity.

TABLE 2

Hydrogenation of 3,7-dimethyloct-6-en-1-yn-3-ol.

| Example | Additive | Amount [mg] | Conversion [%] | Selectivity[2] [%] | Over-Hyd* [%][1] |
|---|---|---|---|---|---|
| Ref.4 | None | | >99.9 | 94.5 | 3.4 |
| Ref.5 | ASP | 45 | 96.8 | 94.7 | 1.9 |
| 9 | AS1 | 28 | >99.9 | 95.9 | 1.6 |
| | AP1 | 81 | | | |
| 10 | AS1 | 28 | >99.9 | 95.8 | 1.6 |
| | AP2 | 61 | | | |
| 11 | AS1 | 28 | >99.9 | 95.9 | 1.7 |
| | AP3 | 64 | | | |

[1]determined by GC in area%

[2]selectivity: amount of alkenol in the final reaction mixture

*Over-Hyd = over-hydrogenation: 3,7-dimethyloct-6-en-3-ol and 3,7-dimethyloct-1-en-3-ol and 3,7-di-methyloctan-3-ol determined by GC in area %

Selective Hydrogenation Series 3:

Hydrogenation of 3,7,11,15-tetramethylhexadec-1-yn-3-ol to 3,7,11,15-tetra-methylhexadec-1-en-3-ol The hydrogenation catalyst (50 mg, palladium-lead on calcium carbonate, containing 5 weight % palladium) was placed in a 500 ml pressure reactor.

The respective additives in the amount as given in table 3 and a total of 260 g 3,7,11,15-tetramethylhexadec-1-yn-3-ol were added to the reactor. The vessel was sealed and purged with nitrogen 3 times (pressurise to 6 bara and release). The reactor was heated to 85° C. and purged with hydrogen 3 times (pressurise to 4 bara and release). The reactor was pressurised to 3 bara and the mixture was stirred. The mixture was sampled multiple times near the end of the reaction to determine when the conversion had reached>99.5%. Samples were analysed by GC (area %) to determine the selectivity.

TABLE 3

Hydrogenation of 3,7,11,15-tetramethylhexadec-1-yn-3-ol.

| Example | Additive | Amount [mg] | Conversion [%] | Selectivity[2] [%][1] | Over-Hyd* [%][1] |
|---|---|---|---|---|---|
| Ref.6 | None | | >99.9 | 88.5 | 8.0 |
| Ref.7 | AP1 | 63 | >99.9 | 92.3 | 4.3 |
| 12 | AS1 | 22 | >99.9 | 95.1 | 1.5 |
| | AP1 | 63 | | | |
| Ref.8 | AP2 | 48 | >99.9 | 92.5 | 4.2 |
| 13 | AS1 | 22 | >99.8 | 94.9 | 1.7 |
| | AP2 | 48 | | | |
| Ref.9 | AP3 | 50 | >99.9 | 92.3 | 4.4 |
| 14 | AS1 | 22 | >99.6 | 94.8 | 1.6 |
| | AP3 | 50 | | | |

[1]determined by GC in area %

[2]selectivity: amount of alkenol in the final reaction mixture

*Over-Hyd = over-hydrogenation: 3,7,11,15-tetra-methylhexadecan-3-ol determined by GC in area %

The invention claimed is:

1. A process for hydrogenating an alkyne selectively to an alkene which comprises subjecting the alkyne to hydrogenation conditions in the presence of a hydrogenation catalyst which is palladium supported on a carrier and in the presence of an additive mixture comprised of an additive AP and an additive AS, wherein (a) the additive AP is an organic phosphorus compound having no sulphur atoms which is selected from the group consisting of triphenylphosphine, 1,2-bis(diphenylphosphino) ethane and 1,3-bis(diphenylphosphino) propane; and (b) the additive AS which is 2,2'-(ethane-1,2-diylbis(sulfanediyl)) bis(ethan-1-ol) of the formula:

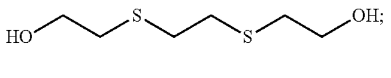

wherein the alkyne comprises at least one carbon-carbon triple bond, and wherein the at least carbon-carbon triple bond is selectively hydrogenated to a respective carbon-carbon double bond to form the alkene.

2. The process according to claim 1, wherein the additive AP and the additive AS are present in a molar ratio of the additive AP to the additive AS of 10:1-1:10.

3. The process according to claim 1, wherein the molar ratio of the additive AP to the additive AS is 5:1-1:5.

4. The process according to claim 1, wherein the molar ratio of the additive AP to the additive AS is 2:1-1:2.

5. The process according to claim 1, wherein the additive mixture and the hydrogenation catalyst are present in a weight ratio of the additive mixture to the hydrogenation catalyst of 0.01:1-100:1.

6. The process according to claim 1, wherein the weight ratio of the additive mixture to the hydrogenation catalyst is 0.1:1-10:1.

7. The process according to claim 1, wherein the weight ratio of the additive mixture to the hydrogenation catalyst is 0.2:1-3:1.

8. The process according to claim 1, wherein the carrier is an oxide or a carbonate.

9. The process according to claim 8, wherein the carrier is an oxide selected from the group consisting of silicon oxide, aluminum oxide, cerium oxide, titanium oxide and calcium carbonate.

10. The process according to claim 1, wherein the hydrogenation is performed in the absence of any organic solvents.

11. The process according to claim 1, wherein the carrier is carbon or an inorganic carrier.

12. The process according to claim 1, wherein the alkyne further comprises at least one chemical functional group, wherein the at least one further chemical functional group remains unchanged by the hydrogenation.

13. The process according to claim 1, wherein the alkyne is an alkynol of the formula (I):

(I)

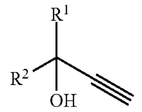

and wherein the alkenol is an alkenol of the formula (II):

(II)

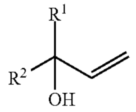

wherein either (1) $R^1$ represents H, a methyl group or an ethyl group; and $R^2$ represents a saturated or unsaturated linear, branched or cyclic hydrocarbyl group with 1 to 46 C atoms which optionally comprises at least one chemical functional group;

or (2) $R^1$ and $R^2$ represent together an alkylene group forming a 5 to 7 membered ring;

with the proviso that $R^1$ has the same meaning in formulae (I) and (II) and that $R^2$ has the same meaning in formulae (I) and (II).

14. The process according to claim 13, wherein $R^2$ is selected from the group consisting of formula (R2-I), (R2-II), (R2-III), (R2-IV), (R2-V), (R2-VI) and (R2-VII), -continued (R2-I)

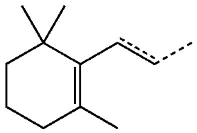

(R2-II)

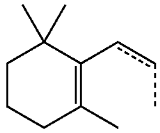

(R2-III)

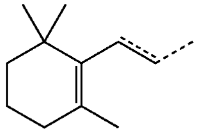

(R2-IV)

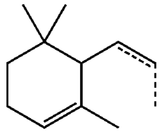

(R2-V)

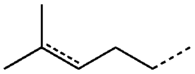

(R2-VI)

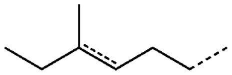

(R2-VII)

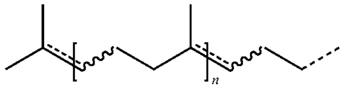

wherein the dotted line represents the bond by which the substituent of formula (R2-I), (R2-II), (R2-III), (R2-IV), (R2-V), (R2-VI) or (R2-VII) is bound to the rest of the compound of formula (I) or formula (II);

and wherein any bond having dotted line ( ) represents independently from each other either a single carbon-carbon bond or a double carbon-carbon bond;

and wherein any wavy line represents independently from each other a carbon-carbon bond which when linked to the carbon-carbon double bond is either in the Z or in the E-configuration;

and wherein n represents 1, 2, 3, 4, 5 or 6.

15. A composition comprising:

(i) an alkyne;

(ii) a hydrogenation catalyst which is palladium supported on a carrier; and (iii) an additive mixture comprised of an additive AP and an additive AS, wherein the additive AP which is an organic phosphorus compound having no sulphur atoms which is selected from the group consisting of triphenylphosphine, 1,2-bis(diphenylphosphino) ethane and 1,3-bis(diphenylphosphino) propane; and wherein the additive AS is an organic sulphur compound having no phosphor atoms which is 2,2'-(ethane-1,2-diylbis(sulfanediyl)) bis(ethan-1-ol) of the formula:

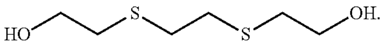

* * * * *